(12) United States Patent
Kondo

(10) Patent No.: US 8,039,665 B2
(45) Date of Patent: Oct. 18, 2011

(54) METHOD FOR PRODUCING FLUORINE-CONTAINING CARBOXYLIC ACID ESTER

(75) Inventor: Takeshi Kondo, Sayama (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 12/665,269

(22) PCT Filed: Jun. 18, 2008

(86) PCT No.: PCT/JP2008/061110
§ 371 (c)(1),
(2), (4) Date: Dec. 17, 2009

(87) PCT Pub. No.: WO2008/156104
PCT Pub. Date: Dec. 24, 2008

(65) Prior Publication Data
US 2010/0197957 A1    Aug. 5, 2010

(30) Foreign Application Priority Data
Jun. 19, 2007    (JP) ................................ 2007-161025

(51) Int. Cl.
*C07C 69/63*    (2006.01)
(52) U.S. Cl. ....................................................... 560/227
(58) Field of Classification Search ........................ None
See application file for complete search history.

(56) References Cited

U.S. PATENT DOCUMENTS

| 2,442,996 A | 6/1948 | Coffman |
| 5,710,317 A | 1/1998 | Oharu et al. |

FOREIGN PATENT DOCUMENTS

| JP | 57-86339 A | 5/1982 |
| JP | 8-92162 A | 4/1996 |
| JP | 2007-70345 A | 3/2007 |

OTHER PUBLICATIONS

White et al, Basic Energy Sciences Advisory Committee Subpanel Workshop Report, Opportunities for Catalysis in the 21st Century, 2002, pp. 1-47.*
Supplementary European Search Report dated May 19, 2010 (six (6) pages).
John A. Young et al., "A New Method of Preparation of Esters of Difluoroacetic Acid", J. Am. Chem. Soc., vol. 72, pp. 1860-1861, Apr. 1950.
V. Tolman, "Preparation of Difluoroacetic Acid and Its Derivatives from Chlorotrlfluoroethylene", Collection Czechoslov. Chem. Commun., vol. 42, pp. 2537-2539, 1977.
Nobuo Ishikawa et al., "Facile Synthesis of Dialkyl Fluoromalonates and Their Derivatives", Chemistry Letters, The Chemical Society of Japan, pp. 107-110, 1981.
International Search Report dated Aug. 12, 2008 w/partial English translation (three (3) pages).

* cited by examiner

*Primary Examiner* — Paul A Zucker
(74) *Attorney, Agent, or Firm* — Crowell & Moring LLP

(57) ABSTRACT

A method for producing a fluorine-containing carboxylic acid ester represented by the general formula $R^1HCFCOOR^2$ involves reacting a fluorine-containing ether represented by the general formula $R^1HCFCF_2OR^2$ with water in the presence of a solid catalyst. The solid catalyst is at least one selected from the group consisting of alumina, titania, zirconia, sulfated zirconia, an activated carbon on which sulfuric acid is supported, a resin having acid sites, and aluminum phosphate. In the general formulas $R^1HCFCOOR^2$ and $R^1HCFCF_2OR^2$, $R^1$ represents a fluorine atom or a $C_{1-4}$ perfluoroalkyl group, and $R^2$ represents a monovalent organic group.

5 Claims, No Drawings

METHOD FOR PRODUCING FLUORINE-CONTAINING CARBOXYLIC ACID ESTER

TECHNICAL FIELD

Fluorine-containing carboxylic acid esters are useful compounds, which are used for catalysts in various reactions, intermediates of medicines and agricultural chemicals, or intermediates of functional materials, etc. The present invention relates to a method for producing a fluorine-containing carboxylic acid ester.

BACKGROUND TECHNIQUE

As a method for producing a fluorine-containing carboxylic acid ester, there are known (1) a method of esterifying a fluorine-containing carboxylic acid in the presence of an acid catalyst, (2) a method of reacting 1-alkoxy-1,1,2,2-tetrafluoroethane, sulfuric acid, and silica (Non-patent Publication 1), (3) a method of reacting difluoroacetic acid fluoride, which is obtained by subjecting 1-alkoxy-1,1,2,2-tetrafluoroethane to a gas-phase reaction in the presence of a metal oxide catalyst, with an alcohol (Patent Publication 1), etc.

In the method of (1), there is a problem that difluoroacetic acid as the raw material is not easily available. As a method for producing difluoroacetic acid, there have been reported (4) a method in which chlorotrifluoroethylene as a starting material is reacted with an alkylamine, followed by hydrolysis to obtain a chlorofluoroacetic amide, moreover fluorination to convert it into difluoroacetic amide, and then hydrolysis (Non-patent Publication 2), (5) a method in which ammonia is added to tetrafluoroethylene to prepare 2,4,6-difluoromethyl-1,3,5-triazine, followed by hydrolysis (Patent Publication 2), etc.

In the method of (4), however, there are problems that the fluorination of chlorofluoroacetic amide is a reaction of a long time and a high temperature, that a post-treatment after the fluorination is complicated, and that yield is also low. Furthermore, in the method of (5), an industrial execution is difficult, since the addition of tetrafluoroethylene and ammonia is a high-pressure reaction of a gauge pressure of 3.4 MPa (34 kgG/cm$^2$).

Furthermore, in each method of (4) and (5), a hydrolysis step is necessary. When using a hydrolysis step using sulfuric acid, there is a problem that a large amount of sulfuric acid waste liquid occurs. Furthermore, in the case of using a hydrolysis step using an alkali metal hydroxide aqueous solution, difluoroacetic acid is obtained as a mixture of water and an inorganic salt. Since difluoroacetic acid has a boiling point higher than that of water, there is a problem that separation from the inorganic salt by distillation is difficult, and recovery is low.

Furthermore, in the method of (2), it is difficult to control the reaction, and there is a risk that the reactor may corrode. Furthermore, the method of (3) is composed of a two-step reaction in which difluoroacetic acid fluoride is once produced from 1-alkoxy-1,1,2,2-tetrafluoroethane, and an alcohol is reacted with it. In more detail, it is composed of complicated steps that the alkoxy group moiety is eliminated as an alcohol by the first step reaction, and the alcohol is again added in the second step. In such reaction process, it is necessary to have a large-scale reaction apparatus and complicated operations. Furthermore, there is a risk that resources may be wasted by dumping a part of the raw material, and an excessive energy may be consumed.

Non-patent Publication 1: J. Am. Chem. Soc., 72, 1860 (1950)
Non-patent Publication 2: Collect. Czech. Chem. Comm., 42(8), 2537 (1977), CS180697
Patent Publication 1: Japanese Patent Application Publication 8-92162
Patent Publication 2: U.S. Pat. No. 2,442,995 specification

DISCLOSURE OF THE INVENTION

Task to be Solved by the Invention

The present invention provides a production method that the target fluorine-containing carboxylic acid ester can be obtained from a fluorine-containing ether by a one-step reaction, that a complicated step and a troublesome operation are not necessary, and that an excessive energy is not consumed.

Means for Solving the Task

The present inventors have repeated eager studies about an advantageous method replacing the above conventional methods. As a result, we have found a method for industrially producing a fluorine-containing carboxylic acid ester with high yield.

That is, the present invention is a method for producing a fluorine-containing carboxylic acid ester represented by the general formula $R^1HCFCOOR^2$ ($R^1$ and $R^2$ represent the same meanings as below) comprising reacting a fluorine-containing ether represented by the general formula $R^1HCFCF_2OR^2$ ($R^1$ represents either of a fluorine atom and a $C_{1-4}$ perfluoroalkyl group, and $R^2$ represents a monovalent organic group) with water in the presence of a solid catalyst.

In the description and the claims of the present invention, the fluorine-containing ether may be written as "HFE".

Advantageous Effect of the Invention

The method for producing a fluorine-containing carboxylic acid ester of the present invention comprises a reaction showing extremely high reactivity and selectivity and makes it possible to obtain a fluorine-containing carboxylic acid ester of high purity. Furthermore, the method of the present invention is a method that makes it possible to produce the target fluorine-containing carboxylic acid ester by a one-step reaction from an industrially available raw material. Furthermore, since the method of the present invention is essentially dehydrofluorination and a transfer reaction in the molecule, it is a method that all the carbons of the ether compound as the raw material can effectively be used as the product. Therefore, the method of the present invention is a method that is industrially extremely superior.

BEST MODE FOR CARRYING OUT THE INVENTION

As the $C_{1-4}$ perfluoroalkyl group in the fluorine-containing ether represented by the general formula $R^1HCFCF_2OR^2$ ($R^1$ represents either of a fluorine atom and a $C_{1-4}$ perfluoroalkyl group, and $R^2$ represents a monovalent organic group), which is the raw material of the present invention, it is possible to cite trifluoromethyl group, pentafluoroethyl group, n-heptafluoropropyl group, heptafluoroisopropyl group, n-nonafluorobutyl group, s-nonafluorobutyl group, and t-nonafluorobutyl group. As $R^1$, a fluorine atom or trifluoromethyl group is particularly preferable.

As the monovalent organic group, it is possible to cite a $C_{1-8}$ alkyl group optionally having a branch, a cycloalkyl group optionally having an alkyl group as a substituent, a fluorine-containing alkyl group, an aryl group, and an aralkyl group. Of these, an alkyl group or fluorine-containing alkyl group is preferable, an alkyl group is more preferable, and a lower alkyl group is still more preferable. The lower alkyl group refers to a $C_{1-4}$ alkyl group.

The $C_{1-8}$ alkyl group optionally having a branch can be exemplified by methyl group, ethyl group, n-propyl group, isopropyl group, n-butyl group, s-butyl group, t-butyl group, n-pentyl group, and isopentyl group.

As the cycloalkyl group optionally having an alkyl group as a substituent, it is possible to cite cyclobutyl group, cyclopentyl group, 2-methylcyclopentyl group, 3-methylcyclopentyl group, 2-ethylcyclopentyl group, 3-ethylcyclopentyl group, cyclohexyl group, 2-methylcyclohexyl group, 3-methylcyclohexyl group, 4-methylcyclohexyl group, 2-ethylcyclohexyl group, 3-ethylcyclohexyl group, 4-ethylcyclohexyl group, cycloheptyl group, 2-methylcycloheptyl group, 3-methylcycloheptyl group, 3-methylcycloheptyl group, 4-methylcycloheptyl group, etc.

The aryl group can be exemplified by phenyl group, 2-methylphenyl group, 3-methylphenyl group, 4-methylphenyl group, 2,3-dimethylphenyl group, 2,4-dimethylphenyl group, 2,5-dimethylphenyl group, 2,6-dimethylphenyl group, 3,4-dimethylphenyl group, 3,5-dimethylphenyl group, 3,6-dimethylphenyl group, 2-methoxyphenyl group, 3-methoxyphenyl group, 4-methoxyphenyl group, 1-naphthyl group, 2-naphthyl group, etc.

The fluorine-containing alkyl group can be exemplified by fluoromethyl group, difluoromethyl group, trifluoromethyl group, chlorofluoromethyl group, chlorodifluoromethyl group, bromofluoromethyl group, dibromofluoromethyl group, 2,2,2-trifluoroethyl group, pentafluoroethyl group, 2,2,3,3,3-pentafluoropropyl group, n-hexafluoropropyl group, hexafluoroisopropyl group, etc.

The aralkyl group can be exemplified by phenethyl group, 2-methylphenylmethyl group, 3-methylphenylmethyl group, 4-methylphenylmethyl group, 2,3-dimethylphenylmethyl group, 2,4-dimethylphenylmethyl group, 2,5-dimethylphenylmethyl group, 2,6-dimethylphenylmethyl group, 3,4-dimethylphenylmethyl group, 3,5-dimethylphenylmethyl group, 3,6-dimethylphenylmethyl group, 4-ethylphenylmethyl group, 4-(n-propyl)methylphenylmethyl group, 4-(n-butyl)methylphenylmethyl group, etc.

It is possible by a publicly known production method to obtain the fluorine-containing ether represented by the general formula $R^1HCFCF_2OR^2$ ($R^1$ represents either a fluorine atom or a $C_{1-4}$ perfluoroalkyl group, and $R^2$ represents a monovalent organic group), which is the raw material of the present invention.

It can be synthesized, for example, by a method of reacting an alcohol compound ($R^2OH$) with a fluorine-containing compound having a double bond, such as tetrafluoroethylene or hexafluoropropene, in the presence of a base.

Specifically, it is possible to synthesize 1-methoxy-1,1,2,2-tetrafluoroethane by a method of reacting methanol with tetrafluoroethylene in the presence of potassium hydroxide (J. Am. Chem. Soc., 73, 1329 (1951)).

Furthermore, it is possible to synthesize 1-hexafluoroisopropyl 1,1,2,3,3,3-hexafluoropropane by a method of reacting hexafluoroisopropanol with hexafluoropropene in the presence of potassium hydroxide (U.S. Pat. No. 3,557,294).

As specific examples of the fluorine-containing ether usable in the present invention, it is possible to cite 1-methoxy-1,1,2,2-tetrafluoroethane, 1-ethoxy-1,1,2,2-tetrafluoroethane, 1-(n-propoxy)-1,1,2,2-tetrafluoroethane, 1-isopropoxy-1,1,2,2-tetrafluoroethane, 1-(n-butoxy)-1,1,2,2-tetrafluoroethane, 1-(s-butoxy)-1,1,2,2-tetrafluoroethane, 1-(t-butoxy)-1,1,2,2-tetrafluoroethane, 1-trifluoromethoxy-1,1,2,2-tetrafluoroethane, 1-difluoromethoxy-1,1,2,2-tetrafluoroethane, 1-(2,2,2-trifluoroethoxy)-1,1,2,2-tetrafluoroethane, 1-pentafluoroethoxy-1,1,2,2-tetrafluoroethane, 1-(2,2,2,3,3-pentafluoropropoxy)-1,1,2,2-tetrafluoroethane, 1-hexafluoroisopropoxy-1,1,2,2-tetrafluoroethane, 1-methoxy-1,1,2,3,3,3-hexafluoropropane, 1-ethoxy-1,1,2,3,3,3-hexafluoropropane, 1-(n-propoxy)-1,1,2,3,3,3-hexafluoropropane, 1-isopropoxy-1,1,2,3,3,3-hexafluoropropane, 1-(n-butoxy)-1,1,2,3,3,3-hexafluoropropane, 1-(s-butoxy)-1,1,2,3,3,3-hexafluoropropane, 1-(t-butoxy)-1,1,2,3,3,3-hexafluoropropane, 1-trifluoromethoxy-1,1,2,3,3,3-hexafluoropropane, 1-difluoromethoxy-1,1,2,3,3,3-hexafluoropropane, 1-(2,2,2-trifluoroethoxy)-1,1,2,3,3,3-hexafluoropropane, 1-pentafluoroethoxy-1,1,2,3,3,3-hexafluoropropane, 1-(2,2,2,3,3-pentafluoropropoxy)-1,1,2,3,3,3-hexafluoropropane, 1-hexafluoroisopropoxy-1,1,2,3,3,3-hexafluoropropane, etc. It is, however, not limited to these.

Water used in the present invention is not particularly limited. Ordinary tap water (tap water) or distilled water, ion exchanged water, and other purified waters are acceptable.

In the present invention, a fluorine-containing ether represented by the general formula $R^1HCFCF_2OR^2$ ($R^1$ represents a fluorine atom or a $C_{1-4}$ perfluoroalkyl group, and $R^2$ represents a monovalent organic group) is reacted with water in the presence of a solid catalyst, thereby producing a fluorine-containing carboxylic acid ester represented by the general formula $R^1HCFCOOR^2$. This reaction is represented by the following formula.

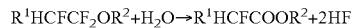

$$R^1HCFCF_2OR^2 + H_2O \rightarrow R^1HCFCOOR^2 + 2HF$$

The solid catalyst is not particularly limited, as long as it is a catalyst that makes the above reaction efficiently proceed. As the solid catalyst, it is possible to use a metal oxide, such as alumina, titania, zirconia, and sulfated zirconia ($ZrO(SO_4)$), an activated carbon on which an inorganic acid, such as sulfuric acid or phosphoric acid, is supported, an activated carbon on which a metal compound is supported, a resin having acid sites, or an inorganic material such as aluminum phosphate ($AlPO_4$).

Alumina used in the present invention is not particularly limited. Normally, it is an alumina obtained by shaping and dehydrating a precipitate produced from an aluminum salt aqueous solution by using ammonia or the like. It is possible to preferably use an γ-alumina on the market for a catalyst support use or a drying use.

Metal oxides, such as titania, zirconia and sulfated zirconia, can also be prepared by similar methods or publicly known methods, and commercial products can also be used. Furthermore, these metal oxides can also be used as complex oxides prepared by a coprecipitation method, etc. Furthermore, it is also possible to support a metal compound by using alumina, titania, zirconia or the like as a support. The type and the amount of the metal to be supported, the supporting method, and the like can be conducted, based on knowledge in the technical field of catalyst, according to the explanation about the after-mentioned activated carbon.

It is possible to prepare an activated carbon, on which sulfuric acid, phosphoric acid or a metal compound is supported, by immersion in sulfuric acid or phosphoric acid or immersion in a solution, in which the metal compound is dissolved, for impregnation, or by spraying to prepare a covered or adsorbed one, and then by drying. In the case of supporting a compound, it can be prepared by impregnation with a solution of the compound or by spraying to prepare a covered or adsorbed one, and then by drying. Furthermore, it is also possible to support a compound that is different from the first compound by making the second compound act on an activated carbon covered or adsorbed by impregnation with a solution of the compound or spraying to generate a precipitation reaction or the like on the activated carbon surface. As a specific example, an activated carbon on which aluminum phosphate is supported is shown in Examples.

The activated carbon can be any of vegetable series using raw materials such as wood, charcoal, coconut husk coal, palm core coal, and raw ash; coal series using raw materials such as peat, lignite, brown coal, bituminous coal, and anthracite; petroleum series using raw materials such as petroleum residue and oil carbon; synthetic resin series using raw materials such as carbonated polyvinylidene chloride. It is possible to use one by selecting from these commercial activated carbons. For example, it is possible to cite an activated carbon produced from bituminous coal (BPL GRANULAR ACTIVATED CARBON made by TOYO CALGON CO.), a coconut husk coal (GRANULAR SHIRO SAGI GX, SX, CX and XRC made by Takeda Chemical Industries, Ltd. and PCB made by TOYO CALGON CO.), etc., but it is not limited to these. It is used generally in the form of granules in terms of shape and size, too. It is possible to use one in the form of sphere, fiber, powder, honeycomb, or the like in an ordinary knowledge scope as long as it fits into the reactor.

The activated carbon used in the present invention is preferably an activated carbon that is large in specific surface area. It is acceptable that the specific surface area and the micropore volume of the activated carbon are in ranges of the standard of commercial products. It is desirable that they are respectively greater than 400 m$^2$/g and greater than 0.1 cm$^3$/g. Furthermore, it is satisfactory that they are respectively 800-3000 m$^2$/g and 0.2-1.0 cm$^3$/g. Furthermore, in the case of using the activated carbon as a support, it is desirable to previously conduct an activation of the support surface and removal of ash by immersing it in a basic aqueous solution, such as ammonium hydroxide, sodium hydroxide, potassium hydroxide, etc., at around ordinary temperature for a period of time of about 10 hours or longer or by conducting a pretreatment by an acid, such as nitric acid, hydrochloric acid, hydrofluoric acid, etc., which is generally conducted upon using activated carbon as a catalyst support.

As a metal compound to be supported, compounds of Al, Ti, Zr, Ce, Cr, Mn, Fe, Co, Ni, Zn, Nb, Sn, Sb, Pb and Bi are preferable. It is preferable that they are water-soluble compounds such as chlorides, bromides, nitrates, etc. Furthermore, these may be alone, or may be supported in a combination of at least two kinds.

Furthermore, as a solid acid catalyst, it is possible to use resins having acid sites, such as perfluorosulfonic acid resins such as Nafion (Nafion, a product of DuPont Co.), cation exchange resins such as Amberlite, Amberjet, Amberlyst, Amberlite XAD and Amberlite CG50 (each is a registered trademark of Rohm and Haas Co.), etc.

Furthermore, a solid catalyst of the present invention may contain other atoms besides a metal component and oxygen. As other atoms, fluorine atom, chlorine atom, etc. are preferable. It may be, for example, a partially fluorinated alumina, a partially chlorinated alumina, a partially fluorochlorinated alumina, a partially fluorinated zirconia, a partially fluorinated titania, etc. The proportion of chlorine atom or fluorine atom in the solid catalyst is not particularly limited.

In the present description and the claims, unless particularly limited, oxides, such as alumina and zirconia, subjected to the above-mentioned partial fluorination, chlorination, etc. are denoted by oxide names such as "alumina" and "zirconia".

As these solid catalysts, at least one metal oxide catalyst selected from the group consisting of alumina ($Al_2O_3$), zirconia ($ZrO_2$) and titania ($TiO_2$) and sulfated zirconia and partially fluorinated oxides of these is preferable. Alumina and a partially fluorinated alumina are more preferable in terms of reactivity and catalyst lifetime.

The solid catalyst is used normally in the form of particles or granulated matter. Diameter of the particles or granulated matter (each may be referred to as "particle size") is not particularly limited. It is normally around 20 μm-10 mm. Furthermore, in case that the solid catalyst contains chlorine atom or fluorine atom, the chlorine atom or fluorine atom may exist only on the surface of the metal oxide catalyst.

It is effective for any solid catalyst to prevent compositional change, lifetime shortening, abnormal reaction, etc. of the catalyst in the reaction by previously bringing it into contact, prior to use, with a fluorine-containing compound such as hydrogen fluoride, a fluorinated hydrocarbon or a fluorochlorinated hydrocarbon or the like to achieve a partial fluorination or partial chlorination.

Furthermore, prior to the reaction, it is preferable to conduct an activation treatment. As the activation treatment, there is applied a normal method that is applied when using a metal oxide catalyst for a fluorination reaction, and it is not particularly limited. As a preferable activation treatment, it is preferable to conduct a sufficient dehydration in a nitrogen stream of about 250° C.-300° C. and an activation with an organic fluorine compound, such as dichlorodifluoromethane and chlorodifluoromethane, or a gas such as hydrogen fluoride or chlorine trifluoride, or an inorganic fluorine compound showing a sufficient vapor pressure under the catalyst treatment condition. This activation treatment is considered to generate an active metal component containing an atom besides the metal component and oxygen, on the surface or entirety of the solid catalyst. Furthermore, it is effective for the prolongation of catalyst lifetime and the improvement of reactivity and reaction yield to supply chlorine, a fluorochlorinated hydrocarbon or chlorinated hydrocarbon, etc. to the reactor during the reaction.

The reaction of the fluorine-containing ether with water in the presence of a solid catalyst uses 0.5-20 mols of water, preferably 1-10 mols of water, relative to 1 mol of the fluorine-containing ether. 1 mol of water is equivalent in the reaction. Less than 0.5 mols of water is not preferable due to low reactivity. It is, however, not limited to this in a production process assuming recovery and reuse. The use exceeding 20 mols is not preferable in terms of both consumption energy and recovery of the product in the production.

The reaction of the fluorine-containing ether ($R^1HCFCF_2OR_2$) with water in the presence of a solid catalyst may either a liquid phase reaction or a gas phase reaction. It is preferably conducted in a gas phase reaction in an industrial production. In the following, conditions and the like regarding the gas phase reaction are explained. It corresponds to design change and is easy for a person skilled in the art to adjust this to conditions and the like of the liquid phase reaction.

In this reaction, it is optional to make an inert gas present. As the inert gas, it is possible to cite nitrogen or rare gas. In terms of handling easiness and availability, nitrogen or helium is preferable. The amount in the case of making an inert gas present is not particularly limited. In case that it is too much, there is a fear of lowering of recovery. Therefore, in normal cases, it is preferable to make an inert gas present to be about 90 volume % or lower in the total amount with a vaporized matter of the fluorine-containing ether of the raw material.

As a reactor for conducting a reaction between the fluorine-containing ether and water in the presence of a solid catalyst, a fixed bed type or fluidized bed type is preferable. The size and shape of the reactor can suitably be changed depending on the type, the amount, and the like of the reactant.

The temperature of the reaction between the fluorine-containing ether and water in the presence of a solid catalyst varies, depending on the type of the catalyst and the raw material. Normally, it is 80-350° C., preferably around 100-300° C., particularly preferably 150-250° C. Low reaction temperature tends to lower conversion. If the reaction temperature exceeds 350° C., by-products of the organic matter may be produced. The reaction time (contact time) is normally 0.1-300 seconds, preferably 1-200 seconds, more preferably 2-60 seconds. In case that the reaction time is overly short too, there is a fear of lowering of conversion. On the other hand, if it is overly long, there is a fear that the production of by-products increases. The reaction pressure is not particularly limited. Any of normal pressure, reduced pressure or pressurization is acceptable. In normal cases, around 0.05-0.5 MPa (0.5-5 atmospheres) is preferable.

In the reaction between the fluorine-containing ether and water in the presence of a solid catalyst of the present invention, hydrogen fluoride is produced as a by-product besides the target fluorine-containing carboxylic acid ester, and it may be accompanied with the unreacted water. Therefore, it is preferable in normal cases to conduct a purification treatment on a crude product obtained by the reaction.

As the treatment of the crude product, there are a method of separation by a direct distillation without conducting other treatments, a method of distilling an organic phase separated by bringing the product into contact with water, and the like. Since the fluorine-containing carboxylic acid ester of the target product has a solubility in water, it is preferable to add an extraction operation in the method of contacting with water.

The reaction between the fluorine-containing ether and water in the presence of a solid catalyst of the present invention shows an extremely high reactivity and is superior in reproducibility of reaction yield, too. Furthermore, it is a reaction in a gas-phase flow continuous system. Therefore, it is efficient and is a reaction superior in terms of productivity, too.

Furthermore, the fluorine-containing carboxylic acid ester ($R^1HCFCOOR^2$) produced by the reaction may contain the corresponding alcohol ($R^2OH$) besides hydrogen fluoride, but it can be removed by contact with water. Furthermore, it is possible to remove $R^2OH$ by bringing a fluorine-containing carboxylic acid fluoride ($R^1HCFCOF$) into contact with the fluorine-containing carboxylic acid ester containing the alcohol ($R^2OH$) in the same reaction apparatus and conditions as those of the method of the present invention to conduct a reaction with the alcohol ($R^2OH$).

The method of bringing the fluorine-containing carboxylic acid fluoride into contact is preferable, particularly in the case of continuously conducting the reaction in an industrial large volume.

The fluorine-containing carboxylic acid ester obtained by the present invention is an extremely useful compound used for various catalysts, intermediates of medicines and agricultural chemicals, and intermediates of functional materials, etc.

In the following, the present invention is specifically explained by citing examples, but the present invention is not limited by these.

EXAMPLE 1

Preparation of Catalyst

A stainless steel reaction tube with a fluorine resin lining, covered with a Nichrome wire heater and a lagging material at its exterior and having an inner diameter of 26 mm and a length of 1000 mm, was charged with 400 cc of γ-alumina (particle size: 3-4 mm). While maintaining the outside temperature at 220° C., hydrogen fluoride made to accompany nitrogen gas was allowed to flow for 6 hours, thereby preparing a partially fluorinated alumina catalyst.

[Reaction]

Then, the reaction tube was made to have a temperature of 180° C. 1-methoxy-1,1,2,2-tetrafluoroethane, together with nitrogen, was introduced at a flow rate of 10.6 gr/Hr into the reaction tube by bubbling nitrogen of about 20 cc/minute through a glass container containing 1-methoxy-1,1,2,2-tetrafluoroethane. Furthermore, at the same time, ion exchanged water was fed at a flow rate of 7.2 gr/Hr with a tube pump into a vaporizing heater maintained at 200° C. for vaporization, and it was introduced into the reaction tube. An effluent from the reaction tube was collected for a period of time of 5 hours after the start of the reaction by a trap containing iced water and a trap cooled with acetone-dry ice. The organic matter and the aqueous layer recovered from both traps were extracted with dibutyl ether, thereby recovering an organic layer. The obtained recovery organic matter was quantitated with a gas chromatograph (FID detector). With this, 1-methoxy-1,1,2,2-tetrafluoroethane of the raw material was not detected, and selectivity of methyl difluoroacetate was 99.2%.

Furthermore, the obtained recovery organic matter was subjected to rectification, thereby obtaining 8.8 g (yield 94.5%) of methyl difluoroacetate of a purity of 99.8% or higher. The results are shown in Table 1.

TABLE 1

| Example | 1 | 2 | 3 | 4 | 5 | 6 | 7 |
|---|---|---|---|---|---|---|---|
| Reaction Temp. (° C.) | 180 | 180 | 180 | 180 | 180 | 180 | 220 |
| Residence Time (s) | 72 | 145 | 72 | 72 | 144 | 116 | 79 |
| Reactivity (%) | 100 | 88.7 | 95.8 | 100 | 98.6 | 90.1 | 100 |
| Selectivity (%) | 99.2 | 99.6 | 99.7 | 99.0 | 99.3 | 98.3 | 89.8 |
| Water/HFE Molar Ratio | 5 | 5 | 5 | 5 | 3 | 2.5 | 5 |
| Yield (%) ※1 | 94.5 | 73.5 | 88.2 | 90.6 | 90.6 | 79.5 | 78.6 |

※1 The yield is a yield of methyl difluoroacetate of a purity of 99.8% or higher obtained by rectification of the recovered organic matter.
The reactivity is a reactivity of HFE (1-methoxy-1,1,2,2-tetrafluoroethane).
The selectivity is a selectivity of methyl difluoroacetate.

EXAMPLE 2

The same reaction was conducted by the same procedure as in Example 1, in a manner that the raw material 1-methoxy-1,1,2,2-tetrafluoroethane was made to have a flow rate of 5.3 gr/Hr by adjusting flow rate of nitrogen gas to about 10 cc/min and that water was made to have a flow rate of 3.6 gr/Hr. The results obtained by running the reaction for 5 hours are shown in Table 1.

EXAMPLE 3

After continuing the reaction under the same conditions as those of Example 1 for 245 hours, the product was recovered for 5 hours. Reactivity of the raw material 1-methoxy-1,1,2,2-tetrafluoroethane and selectivity of methyl difluoroacetate were determined. The results are shown in Table 1. Activity lowering of the catalyst was almost not found.

EXAMPLE 4

After terminating the reaction of Example 3, the catalyst having a thin coking was taken out of the reaction tube used in the reaction. It was transferred to a reaction tube that was equipped with an electric furnace at exterior, had an inner diameter of 4.2 cm and a length of 60 cm, and was made of SUS304. While the air was allowed to flow, the temperature of the electric furnace was increased to 600° C., and it was maintained at that temperature for 5 hours. After cooling to room temperature, the catalyst was again returned to the reaction tube with a fluorine resin lining, used in Example 1. The temperature of the reaction tube was changed to 220° C., and, while maintaining that temperature, a pretreatment of the catalyst was conducted by allowing hydrogen fluoride, made to accompany nitrogen gas, to flow at a flow rate of 20 g/Hr for 2 hours. Then, the reaction was conducted under the same conditions as those of Example 1. With this, almost the same results as those of Example 1 were obtained. The results are shown in Table 1.

EXAMPLE 5

The same reaction was conducted by the same procedure as in Example 1, in a manner that the raw material 1-methoxy-1,1,2,2-tetrafluoroethane was made to have a flow rate of 7.7 gr/Hr by adjusting flow rate of nitrogen gas to about 14.5 cc/min and that water was made to have a flow rate of 3.1 gr/Hr. The results obtained by running the reaction for 5 hours are shown in Table 1.

EXAMPLE 6

The same reaction was conducted under the same procedure as in Example 1 by adjusting the flow rate of the raw material 1-methoxy-1,1,2,2-tetrafluoroethane to 10.6 gr/Hr and the flow rate of the water to 3.6 gr/Hr. The results obtained by running the reaction for 5 hours are shown in Table 1. Lowering of reactivity is found in Example 6, in which the molar ratio of water/1-methoxy-1,1,2,2-tetrafluoroethane was lowered (the molar ratio: 2.5), as compared with Example 1 (the molar ratio: 5), but a high yield of 79.5% was obtained.

EXAMPLE 7

The same reaction was conducted under the conditions of Example 1, except in that the reaction temperature was adjusted to 220° C. The results are shown in Table 1. Selectivity of methyl difluoroacetate was somewhat low.

EXAMPLE 8

Synthesis of Ethyl Difluoroacetate

The reaction was conducted by the same procedure as that of Example 1 under the conditions shown in Table 2, in which 1-ethoxy-1,1,2,2-tetrafluoroethane (11.7 gr/Hr) was used as the raw material in place of 1-methoxy-1,1,2,2-tetrafluoroethane and in which the flow rate of the water was adjusted to 7.2 gr/Hr. The results are shown in Table 2.

TABLE 2

|  | Example | |
| --- | --- | --- |
|  | 8 | 9 |
| Reaction Temp. (° C.) | 180 | 160 |
| Residence Time (s) | 73 | 76 |
| Reactivity (%) | 100 | 72.3 |
| Selectivity (%) | 99.5 | 99.5 |
| Water/HFE Molar Ratio | 5 | 5 |

※ The reactivity is a reactivity of HFE (1-ethoxy-1,1,2,2-tetrafluoroethane).
The selectivity is a selectivity of ethyl difluoroacetate.

EXAMPLE 9

The same reaction was conducted under the conditions of Example 8, except in that the reaction temperature was adjusted to 160° C. The results are shown in Table 2.

EXAMPLE 10

The reaction was conducted by the same procedure as that of Example 1 under the conditions shown in Table 3, in which 1-methoxy-1,1,2,3,3,3-hexafluoropropane (14.6 gr/Hr) was used as the raw material in place of 1-methoxy-1,1,2,2-tetrafluoroethane and in which the flow rate of the water was adjusted to 7.2 gr/Hr. The results are shown in Table 3.

TABLE 3

|  | Example | |
| --- | --- | --- |
|  | 10 | 11 |
| Reaction Temp. (° C.) | 180 | 220 |
| Residence Time (s) | 72 | 66 |
| Reactivity (%) | 100 | 100 |
| Selectivity (%) | 99.3 | 85.3 |
| Water/HFE Molar Ratio | 5 | 5 |

※ The reactivity is a reactivity of HFE (1-methoxy-1,1,2,3,3,3-hexafluoropropane).
The selectivity is a selectivity of methyl 2,3,3,3-tetrafluoropropionate.

EXAMPLE 11

The same reaction was conducted under the conditions of Example 11, except in that the reaction temperature was adjusted to 220° C. The results are shown in Table 3.

EXAMPLE 12

A pretreatment was conducted by the same procedure as that of Example 1, except in that 400 cc of zirconia was used in place of 400 cc of γ-alumina. Then, the reaction was conducted at 200° C. by the same procedure as that of Example 1 under conditions shown in Table 4. With this, the formation of methyl difluoroacetate was found. The results are shown in Table 4.

TABLE 4

|  | Example | |
| --- | --- | --- |
|  | 12 | 13 |
| Reaction Temp. (° C.) | 200 | 220 |
| Residence Time (s) | 69 | 66 |
| Reactivity (%) | 92.5 | 97.2 |
| Selectivity (%) | 98.8 | 83.7 |
| Water/HFE Molar Ratio | 5 | 5 |

※ The reactivity is a reactivity of HFE (1-methoxy-1,1,2,2-tetrafluoroethane).
The selectivity is a selectivity of methyl difluoroacetate.

EXAMPLE 13

The same reaction was conducted under conditions of Example 12, except in that the reaction temperature was adjusted to 220° C. The results are shown in Table 4.

EXAMPLES 14 & 15

Experiments were conducted under the same reaction conditions as those of Example 1, except in that, there was used as the catalyst 400 cc of aluminum phosphate tablets having a diameter of about 3 mm and shaped from a powder obtained by a method described in a publication (Applied Catalyst A: General 283 (2005) 47-52), in place of γ-alumina. They were conducted at reaction temperatures of 180° C. and 200° C. The results are shown in Table 5.

TABLE 5

|  | Example | |
| --- | --- | --- |
|  | 14 | 15 |
| Reaction Temp. (° C.) | 180 | 200 |
| Residence Time (s) | 72 | 69 |
| Reactivity (%) | 98.8 | 99.7 |
| Selectivity (%) | 99.5 | 88.4 |
| Water/HFE Molar Ratio | 5 | 5 |

※ The reactivity is a reactivity of HFE (1-methoxy-1,1,2,2-tetrafluoroethane).
The selectivity is a selectivity of methyl difluoroacetate.

EXAMPLES 16 & 17

400 cc of SHIRO SAGI G2C (4-8 mesh, a product of Takeda Chemical Industries, Ltd.) was immersed under room temperature for one night in a 10 mass weight percent aluminum nitrate aqueous solution for impregnation. Then, an equivalent of 85% phosphoric acid was added, and 10% aqueous ammonia was added dropwise with stirring. The dropping was terminated at a pH of 5. An aluminum phosphate-supported activated carbon was obtained by separating the activated carbon from the solution, in which aluminum phosphate was precipitated, with a resin-made net. Most of water was removed from this by a drier of 120° C. Then, it was baked for 2 hours in a baking furnace of nitrogen atmosphere set at 400° C., thereby preparing an aluminum phosphate-supported activated carbon supporting aluminum phosphate in 15 weight %.

Experiments were conducted under the same reaction conditions as those of Example 1, except in that 400 cc of this aluminum phosphate-supported activated carbon was used in place of γ-alumina. They were conducted at reaction temperatures of 180° C. and 200° C. The results are shown in Table 6.

TABLE 6

|  | Example | |
| --- | --- | --- |
|  | 16 | 17 |
| Reaction Temp. (° C.) | 180 | 200 |
| Residence Time (s) | 72 | 69 |
| Reactivity (%) | 99.3 | 100 |
| Selectivity (%) | 99.3 | 92.1 |
| Water/HFE Molar Ratio | 5 | 5 |

※ The reactivity is a reactivity of HFE (1-methoxy-1,1,2,2-tetrafluoroethane).
The selectivity is a selectivity of methyl difluoroacetate.

EXAMPLES 18 & 19

Experiments were conducted under the same reaction conditions as those of Example 1, except in that 400 cc of 7-9 mesh Nafion NR50 (a product of DuPont Co.) was used in place of γ-alumina. They were conducted at reaction temperatures of 160° C. and 180° C. The results are shown in Table 7.

TABLE 7

|  | Example | |
| --- | --- | --- |
|  | 18 | 19 |
| Reaction Temp. (° C.) | 160 | 180 |
| Residence Time (s) | 76 | 72 |
| Reactivity (%) | 73.3 | 85.3 |
| Selectivity (%) | 99.5 | 82.1 |
| Water/HFE Molar Ratio | 5 | 5 |

※ The reactivity is a reactivity of HFE (1-methoxy-1,1,2,2-tetrafluoroethane).
The selectivity is a selectivity of methyl difluoroacetate.

EXAMPLES 20 & 21

A 2000 ml glass beaker was charged with 700 ml of distilled water and 302 g of ammonium sulfate, followed by stirring at room temperature, thereby obtaining a colorless transparent solution. To this, 1367.6 g of zirconium hydroxide was added with stirring, and stirring was further conducted for 1 hour. Then, the reaction mixture was subjected to evaporation to dryness by a hot plate. The obtained cake was dried in the air at room temperature for 20 hours, thereby obtaining a white-color solid. The obtained white-color solid was baked at 550° C. for 3 hours in the air. This baked material was ground and sieved to prepare a 4-8 mesh sulfated zirconia.

Except in that 400 cc of this sulfated zirconia was used in place of 400 cc of γ-alumina, experiments were conducted under the same reaction conditions as those of Example 1. The results are shown in Table 8.

TABLE 8

|  | Example | |
| --- | --- | --- |
|  | 20 | 21 |
| Reaction Temp. (° C.) | 180 | 200 |
| Residence Time (s) | 72 | 69 |
| Reactivity (%) | 98.8 | 99.7 |
| Selectivity (%) | 92.2 | 88.4 |
| Water/HFE Molar Ratio | 5 | 5 |

※ The reactivity is a reactivity of HFE (1-methoxy-1,1,2,2-tetrafluoroethane).
The selectivity is a selectivity of methyl difluoroacetate.

EXAMPLE 22

800 cc of an activated carbon (SHIRO SAGI G2C, 4-8 mesh) was immersed in a glass beaker containing 400 cc of 98% concentrated sulfuric acid, and it was left for one night as it was. Then, it was taken out, and an excessive sulfuric acid was drained. After that, it was put into a reaction tube used in Example 1. While nitrogen gas was allowed to flow, the temperature of the reaction tube was increased to 200° C. and maintained for 3 hours as it was, thereby preparing a sulfuric acid-supported activated carbon.

The temperature of the reaction tube was adjusted to 180° C., and a reaction was conducted under the same conditions as those of Example 1. The results are shown in Table 9.

TABLE 9

|  | Example 22 |
| --- | --- |
| Reaction Temp. (° C.) | 180 |
| Residence Time (s) | 72 |
| Reactivity (%) | 91.3 |
| Selectivity (%) | 84.2 |
| Water/HFE Molar Ratio | 5 |

※ The reactivity is a reactivity of HFE (1-methoxy-1,1,2,2-tetrafluoroethane).
The selectivity is a selectivity of methyl difluoroacetate.

INDUSTRIAL APPLICABILITY

The reaction of the present invention is a superior reaction that shows extremely high reactivity and selectivity and that is also high in reproducibility of the reaction results. Furthermore, the reaction is an appropriate method as an industrial production method too, since it can be conducted continuously and quantitatively. Furthermore, the reaction of the present invention is a highly practical method, since it can be conducted under safe conditions.

The invention claimed is:

1. A method for producing a fluorine-containing carboxylic acid ester represented by the general formula $R^1HCFCOOR^2$ where $R^1$ represents a fluorine atom or a $C_{1-4}$ perfluoroalkyl group, and $R^2$ represents a monovalent organic group, the method comprising reacting a fluorine-containing ether represented by the general formula $R^1HCFCF_2OR^2$ where $R^1$ and $R^2$ are defined as above, with water in the presence of a solid catalyst, wherein the solid catalyst is at least one selected from the group consisting of alumina, titania, zirconia, sulfated zirconia, an activated carbon on which sulfuric acid is supported, a resin having acid sites, and aluminum phosphate.

2. The method according to claim 1, wherein the solid catalyst is alumina.

3. The method according to claim 1, wherein the solid catalyst is alumina, titania, zirconia, or sulfated zirconia in which at least a part of oxygen bonded to the aluminum, titanium, or zirconium has been replaced with fluorine prior to the reaction or in the reaction.

4. The method according to claim 1, which is conducted in a gas phase.

5. The method according to claim 1, wherein $R^1$ is either of a fluorine atom and a trifluoromethyl group.

* * * * *